US011406442B2

(12) United States Patent
Davison et al.

(10) Patent No.: US 11,406,442 B2
(45) Date of Patent: Aug. 9, 2022

(54) ARTICULATE WRIST WITH FLEXIBLE CENTRAL MEMBER

(71) Applicant: Ethicon LLC, Guaynabo, PR (US)

(72) Inventors: Mark A. Davison, Maineville, OH (US); Christopher W. Birri, West Chester, OH (US); William George Saulenas, Cincinnati, OH (US); Jalen Lee Wize, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 736 days.

(21) Appl. No.: 16/180,280

(22) Filed: Nov. 5, 2018

(65) Prior Publication Data

US 2020/0138508 A1    May 7, 2020

(51) Int. Cl.
*A61B 18/14*    (2006.01)
*A61B 34/30*    (2016.01)
(Continued)

(52) U.S. Cl.
CPC ...... *A61B 18/1445* (2013.01); *A61B 18/1206* (2013.01); *A61B 18/16* (2013.01); *A61B 34/30* (2016.02); *A61B 34/71* (2016.02); *A61B 2018/0063* (2013.01); *A61B 2018/126* (2013.01); *A61B 2018/1452* (2013.01); *A61B 2018/162* (2013.01); *A61B 2034/306* (2016.02)

(58) Field of Classification Search
CPC . A61B 18/1445; A61B 18/1206; A61B 18/16; A61B 34/30; A61B 34/71; A61B 2018/0063; A61B 2018/126; A61B 2018/1452; A61B 2018/162; A61B 2034/306
See application file for complete search history.

(56) References Cited

U.S. PATENT DOCUMENTS

| 8,333,780 B1 | 12/2012 | Pedros et al. |
| 2003/0036748 A1* | 2/2003 | Cooper ................. A61B 34/71 606/1 |

(Continued)

FOREIGN PATENT DOCUMENTS

| EP | 2489318 B1 | 8/2012 |
| EP | 3321047 A1 | 5/2018 |
| WO | 2016186999 A1 | 11/2016 |

OTHER PUBLICATIONS

ISR-WO for related application PCT/IB2019/059150 dated Jan. 27, 2020.

*Primary Examiner* — Michael F Peffley
*Assistant Examiner* — Bo Ouyang
(74) *Attorney, Agent, or Firm* — Vorys, Sater, Seymour and Pease LLP

(57) ABSTRACT

An articulable wrist for an end effector includes a distal linkage provided at a distal end of the articulable wrist, a proximal linkage provided at a proximal end of the articulable wrist, and a central channel cooperatively defined by the distal and proximal linkages and extending between the distal and proximal ends. A flexible member is arranged within the central channel and has a first end operatively coupled to the distal linkage and a second end axially movable relative to the proximal linkage. One or more conduits are defined in the flexible member to receive one or more central actuation members extending through the flexible member.

19 Claims, 6 Drawing Sheets

(51) Int. Cl.
    *A61B 34/00*     (2016.01)
    *A61B 18/12*     (2006.01)
    *A61B 18/16*     (2006.01)
    *A61B 18/00*     (2006.01)

(56) References Cited

U.S. PATENT DOCUMENTS

| | | |
|---|---|---|
| 2004/0193146 A1 | 4/2004 | Lee |
| 2011/0087221 A1 | 4/2011 | Siebrecht et al. |
| 2014/0107667 A1 | 4/2014 | Komuro et al. |
| 2017/0095922 A1* | 4/2017 | Licht .................. A61B 34/30 |
| 2017/0252096 A1 | 9/2017 | Felder et al. |
| 2018/0206904 A1 | 7/2018 | Felder et al. |
| 2018/0311471 A1 | 11/2018 | Kampa et al. |

\* cited by examiner

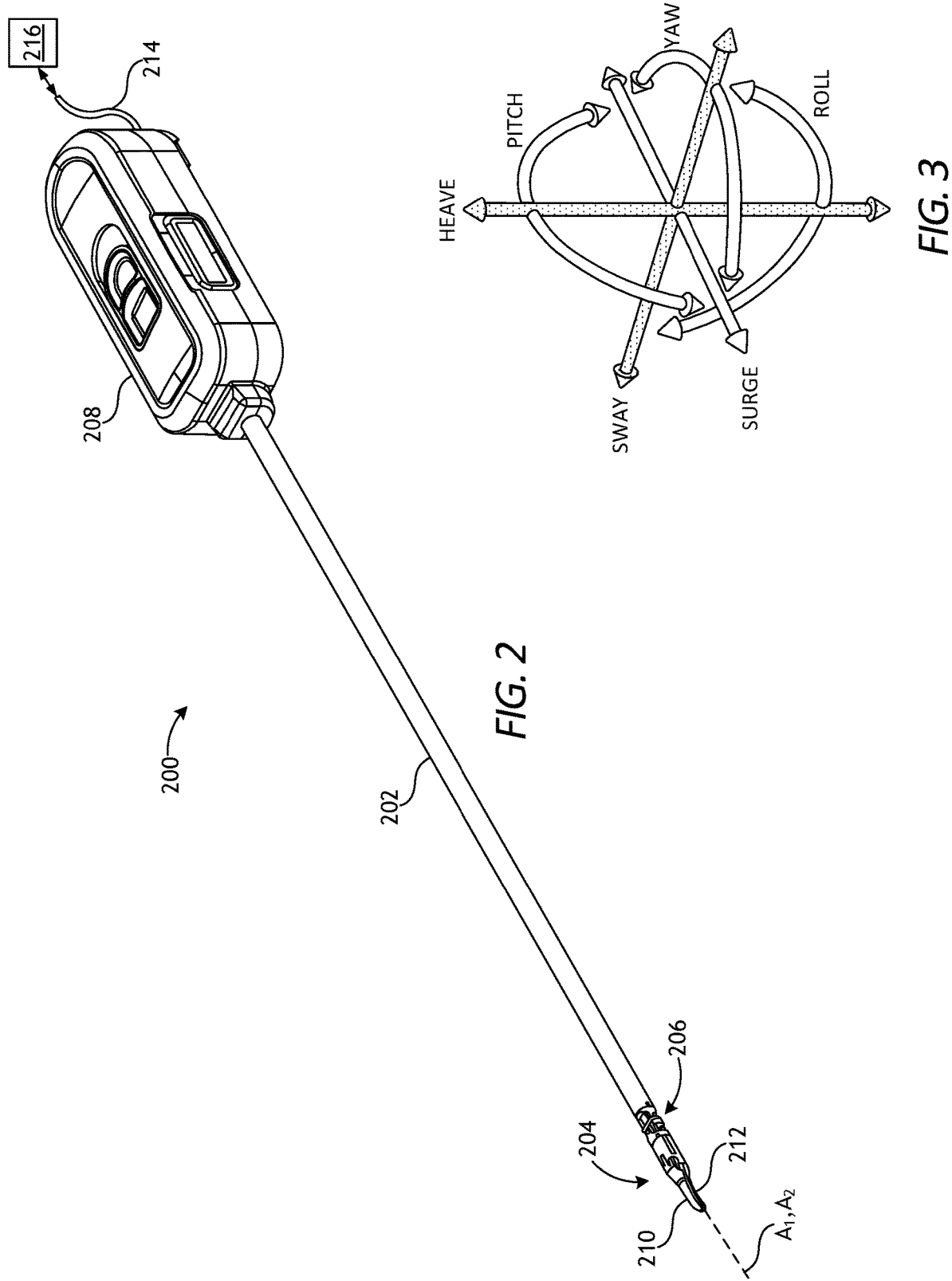

ARTICULATE WRIST WITH FLEXIBLE CENTRAL MEMBER

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

As the wrist joint articulates, drive cables and other elongate members that pass through the wrist joint change length as they are stretched in tension or slackened, depending on the degree of articulation and the offset of the drive cable from the central axis. Upon articulation, for example, drive cables closer to the top of the articulated curvature (e.g., most convex section of the wrist) may be stretched and extended in tension, while drive cables angularly opposite closer to the bottom of the articulated curvature (e.g., most concave section of the wrist) may be slackened. Changing the lengths of the drive cables or other elongate members introduces unpredictability of the true location of each drive cable, which can affect efficient operation of the end effector.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2 is an isometric side view of an example surgical tool that may incorporate some or all of the principles of the present disclosure.

FIG. 3 illustrates potential degrees of freedom in which the wrist of the surgical tool of FIG. 2 may be able to articulate (pivot) or translate.

DETAILED DESCRIPTION

The present disclosure is related to robotic surgical systems and, more particularly, to end effectors with articulable wrists that include a flexible member extending through the articulable wrists and accommodating one or more central actuation members.

Embodiments described herein disclose surgical tools that may include a drive housing, an elongate shaft that extends from the drive housing, and an end effector arranged at an end of the elongate shaft. An articulable wrist may interpose the end effector and the elongate shaft and may including a distal linkage provided at a distal end of the articulable wrist and operatively coupled to the end effector, and a proximal linkage provided at a proximal end of the articulable wrist and operatively coupled to the elongate shaft. A central channel may be cooperatively defined by the distal and proximal linkages and extend between the distal and proximal ends. A flexible member may be arranged within the central channel and may have a first end operatively coupled to the distal linkage and a second end axially movable relative to the proximal linkage. One or more central actuation members may extend from the drive housing and through the flexible member via one or more conduits (i.e., lumens) defined in the flexible member. As the wrist articulates, the flexible member may be able to correspondingly bend or flex, and the central actuation members will correspondingly move in the direction of articulation and thereby lengthen or shorten.

Incorporation of the flexible member having defined conduits to guide the central actuation members (e.g., drive cables) creates distinct and repeatable pathways thus improving the ability to predict cable length and location. Just as the cables change length with articulation so will the flexible member. Constraint of both ends of the flexible member during articulation would put it in compression which may cause kinking or obstruction of the inner conduits that may restrict the movement of the drive cables. Fixing one end of the flexible member and allowing the opposite end to translate longitudinally along the shaft axis enables the flexible member to move relative to the articulation joints thus keeping the integrity of the inner conduits intact. Moreover, fixing the flexible member at or near the distal end of the wrist, however, effectively provides a fixed and known location where the central actuation members exit the wrist.

Figure 1:
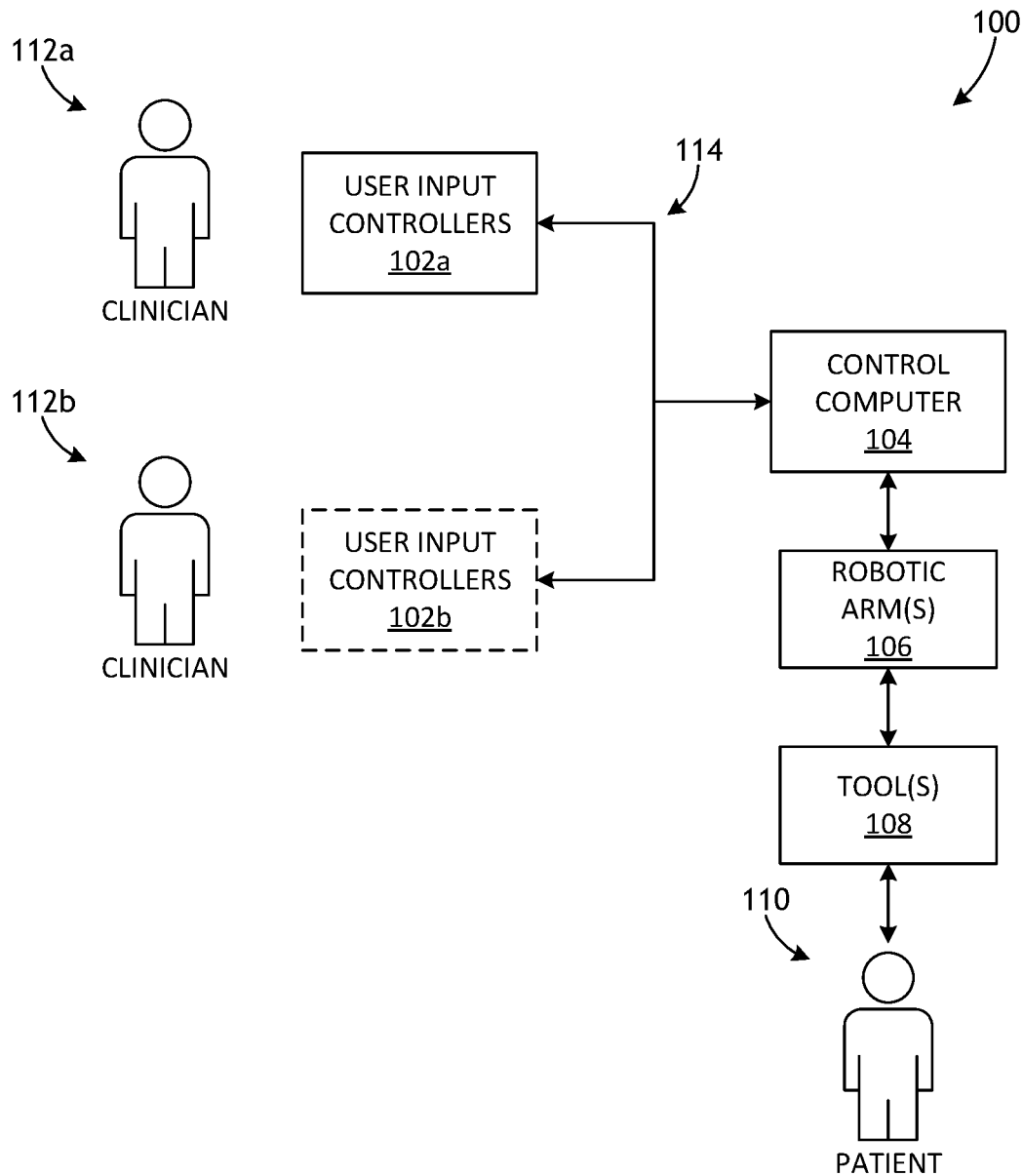
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112a,b via a display to provide a visual indication of various surgical instrument metrics, such as the amount of force being applied to the surgical instrument (i.e., a cutting instrument or dynamic clamping member).

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, rotation, articulation, cutting, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The surgical tool 200 can have any of a variety of configurations capable of performing at least one surgical function. For example, the surgical tool 200 may include, but is not limited to, forceps, a grasper, a needle driver, scissors, an electro cautery tool, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can have a variety of sizes, shapes, and configurations. In the illustrated embodiment, the end effector 204 comprises a tissue grasper and vessel sealer that include opposing jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions. It is noted, however, that the principles of the present disclosure are equally applicable to an end effector that does not include opposing jaws.

FIG. 3 illustrates the potential degrees of freedom in which the wrist 206 may be able to articulate (pivot). The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 204) with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate movement and articulation of the end effector 204 relative to the shaft 202. Moving (actuating) at least some of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

Figure 4:
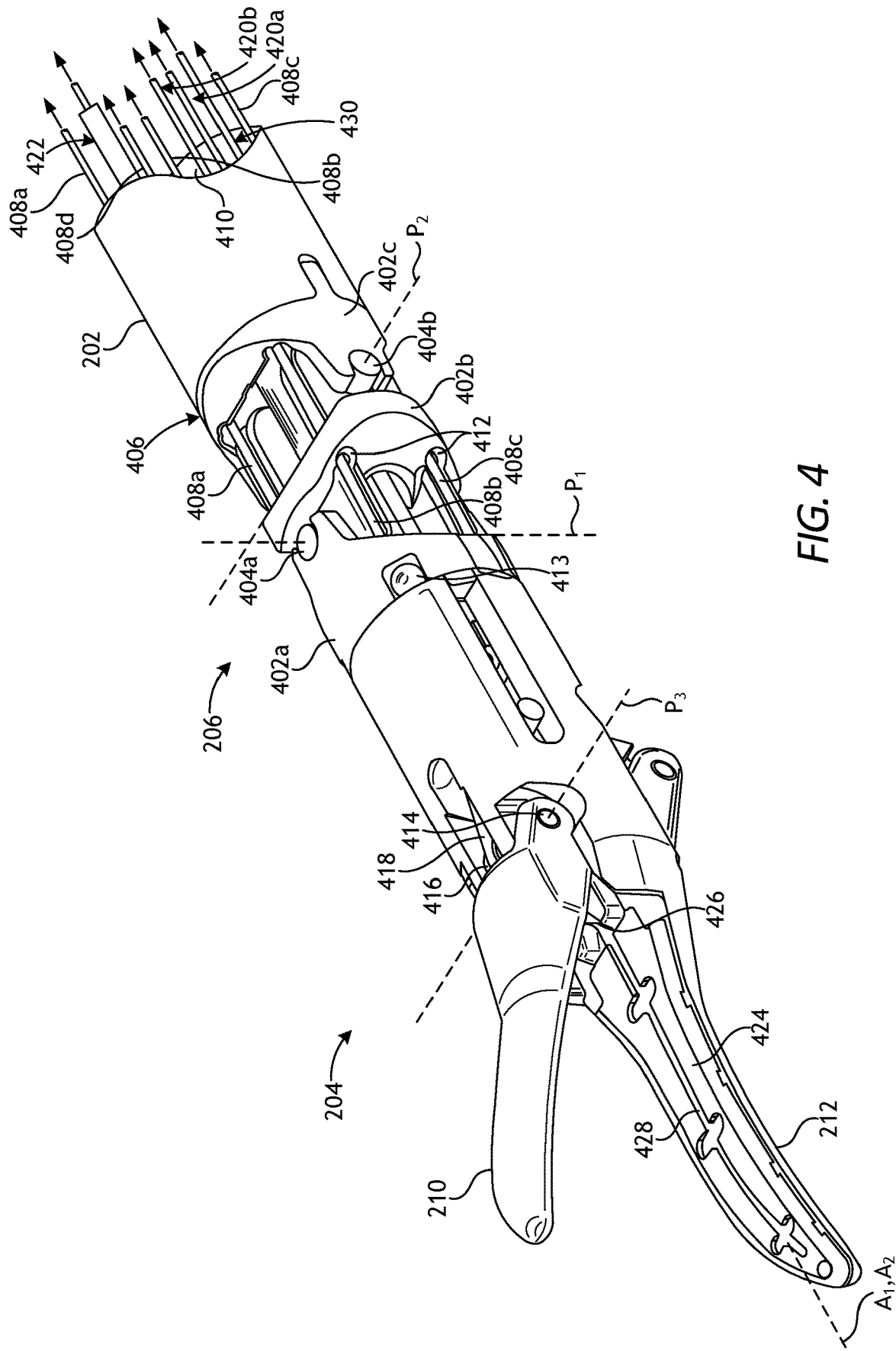
FIG. 4 is an enlarged isometric view of the distal end of the surgical tool of FIG. 2.

FIG. 4 is an enlarged isometric view of the distal end of the surgical tool 200 of FIG. 2. More specifically, FIG. 4 depicts an enlarged view of the end effector 204 and the wrist 206, with the jaws 210, 212 of the end effector 204 in the open position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" linkage 402a, a second or "intermediate" linkage 402b, and a third or "proximal" linkage 402c. The linkages 402a-c are configured to facilitate articulation of the end effector 204 relative to the elongate shaft 202, e.g., angle the end effector 204 relative to the longitudinal axis $A_1$ of the shaft 202. In the illustrated embodiment, articulation via the linkages 402a-c may be limited to pitch only, yaw only, or a combination thereof. As illustrated, the distal end of the distal linkage 402a may be coupled to the end effector 204 and, more particularly, to the lower jaw 212 (or an extension of the lower jaw 212). The proximal end of the distal linkage 402a may be rotatably coupled to the intermediate linkage 402b at a first axle 404a, and the intermediate linkage 402b may also be rotatably coupled to the proximal linkage 402c at a second axle 404b. The proximal end of the proximal linkage 402c may be coupled to a distal end 406 of the shaft 202 (or alternatively a shaft adapter).

The wrist 206 provides a first pivot axis $P_1$ that extends through the first axle 404a and a second pivot axis $P_2$ that extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. Alternatively, the first pivot axis $P_1$ could be configured to provide "pitch" articulation and the second pivot axis $P_2$ could be configured to provide "yaw" articulation.

A plurality of drive cables, shown as drive cables 408a, 408b, 408c, and 408d, extend longitudinally within a lumen 410 defined by the shaft 202 (and/or a shaft adaptor) and pass through the wrist 206 to be operatively coupled to the end effector 204. The lumen 410 can be a single lumen, as illustrated, or can alternatively comprise a plurality of independent lumens, where each lumen receives one or more of the drive cables 408a-d.

The drive cables 408a-d form part of the cable driven motion system briefly described above, and may be referred to and otherwise characterized as cables, bands, lines, cords, wires, woven wires, ropes, strings, twisted strings, elongate members, etc. The drive cables 408a-d can be made from a variety of materials including, but not limited to, metal (e.g., tungsten, stainless steel, etc.) a polymer (e.g., ultra-high molecular weight polyethylene), a synthetic fiber (e.g., KEVLAR®, VECTRAN®, etc.), or any combination thereof. While four drive cables 408a-d are depicted in FIG. 4, more or less than four drive cables 408a-d may be included, without departing from the scope of the disclosure.

The drive cables 408a-d extend proximally from the end effector 204 to the drive housing 208 (FIG. 2) where they are operatively coupled to various actuation mechanisms (e.g., capstans) or devices housed therein to facilitate longitudinal movement (translation) of the drive cables 408a-d within the lumen 410. Selective actuation of all or a portion of the drive cables 408a-d causes the end effector 204 to articulate (pivot) relative to the shaft 202. More specifically, selective actuation causes a corresponding drive cable 408a-d to translate longitudinally within the lumen 410 and thereby cause pivoting movement of the end effector 204. Moving the drive cables 408a-d can be accomplished in a variety of ways, such as by triggering an associated actuator or mechanism (e.g., a capstan) operatively coupled to or housed within the drive housing 208 (FIG. 2). Moving a given drive cable 408a-d constitutes applying tension (i.e., pull force) to the given drive cable 408a-d in a proximal direction, which causes the given drive cable 408a-d to translate and thereby cause the end effector 204 to move (articulate) relative to the shaft 202. As will be appreciated, applying tension to and moving one drive cable 408a-d may result in the slackening of a drive cable 402a-d angularly (or diagonally) opposite to the moving drive cable 402a-d.

The drive cables 408a-d each extend longitudinally through the first, second, and third linkages 402a-c. In some embodiments, each linkage 402a-c may define four, equidistantly-spaced apertures 412 (only two labeled) configured to guide the drive cables 408a-d through the wrist 206. The apertures 412 of each linkage 402a-c may coaxially align when the end effector 204 is in the unarticulated position. The apertures 412 may provide rounded edges and sufficiently large radii to help reduce friction between the drive cables 408a-d and the linkages 402a-c and/or help prevent the drive cables 408a-d from twisting or moving radially inward or outward during articulation.

In some embodiments, the distal end of each drive cable 408a-d may terminate at the distal linkage 402a, thus operatively coupling each drive cable 408a-d to the end effector 204 and, more particularly, to the lower jaw 212. The distal end of each drive cable 408a-d may be enlarged to facilitate fixed attachment thereof to the end effector 204. In some embodiments, as illustrated, the distal end of each drive cable 408a-d may include a ball crimp 413 (only one shown). In other embodiments, however, the distal end of each drive cable 408a-d may include a weld, an adhesive attachment, a press fit, or any combination of the foregoing.

The jaws 210, 212 may be moved between the closed and open positions by pivoting the upper jaw 210 relative to the lower jaw 212. In the illustrated embodiment, the upper jaw 210 may be rotatably coupled (mounted) to the lower jaw 212 at a jaw axle 414. A third pivot axis $P_3$ extends through the jaw axle 414 and is generally perpendicular (orthogonal) to the first pivot axis $P_1$ and parallel to the second pivot axis $P_2$. In this embodiment, the lower jaw 212 remains stationary as the upper jaw 210 pivots about the third pivot axis $P_3$. In other embodiments, however, the jaws 210, 212 may be moved between the closed and open positions by moving (pivoting) both jaws 210, 212, without departing from the scope of the disclosure.

A central pulley 416 (partially visible) may be mounted to the jaw axle 414 and receive a jaw cable 418 that may be actuated to selectively open and close the jaws 210, 212. Similar to the drive cables 408a-d, the jaw cable 418 extends longitudinally within the lumen 410 and passes through the wrist 206. The jaw cable 418 may form part of the cable driven motion system described herein and, therefore, may extend proximally from the end effector 204 to the drive housing 208 (FIG. 2). The jaw cable 418 may comprise a single line or wire looped around the central pulley 416 and opposing first and second ends 420a and 420b of the jaw cable 418 extend proximally to the drive housing 208. The ends 420a,b of the jaw cable 418 may be operatively coupled to individual (discrete) actuation mechanisms (e.g., two capstans) housed within the drive housing 208. Actuation of corresponding drive inputs associated with each actuation mechanism will cooperatively cause tension or slack in the jaw cable 418 and thereby cause the upper jaw 210 to rotate about the third pivot axis $P_3$ between the open and closed positions.

In some embodiments, an electrical conductor 422 may supply electrical energy to the end effector 204 and, more particularly, to an electrode 424 included in the end effector 204. The electrical conductor 422 extends longitudinally within the lumen 410, through the wrist 206, and terminates at the electrode 424. In the illustrated embodiment, the electrode 424 is mounted to (e.g., overmolded onto) or otherwise forms part of the lower jaw 212. In other embodiments, however, the electrode 424 may form part of the upper jaw 210, or may alternatively be coupled to or form part of both jaws 210, 212, without departing from the scope of the disclosure. In some embodiments, the electrical conductor 422 and the power cable 214 (FIG. 2) may comprise the same structure. In other embodiments, however, the electrical conductor 422 may be electrically coupled to the power cable 214, such as at the drive housing 208 (FIG. 2). In yet other embodiments, the electrical conductor 422 may extend to the drive housing 208 where it is electrically coupled to an internal power source, such as batteries or fuel cells.

In some embodiments, the electrical conductor 422 may comprise a wire. In other embodiments, however, the electrical conductor 422 may comprise a rigid or semi-rigid shaft, rod, or strip (ribbon) made of a conductive material. The electrical conductor 422 may be partially covered with an insulative covering (overmold) made of a non-conductive material. The insulative covering, for example, may comprise a plastic applied to the electrical conductor 422 via heat shrinking, but could alternatively be any other non-conductive material.

The end effector 204 may be configured for monopolar or bipolar operation. In at least one embodiment, the electrical energy conducted through the electrical conductor 422 may comprise radio frequency ("RF") energy exhibiting a frequency between about 100 kHz and 1 MHz. In a process known as Joule heating (resistive or Ohmic heating) the RF energy is transformed into heat within the target tissue due the tissue's intrinsic electrical impedance, thereby increasing the temperature of target tissue. Accordingly, heating of the target tissue is used to achieve various tissue effects such as cauterization and/or coagulation and thus may be particularly useful for sealing blood vessels or diffusing bleeding during a surgical procedure.

In the illustrated embodiment, the end effector 204 comprises a combination tissue grasper and vessel sealer that includes a cutting element 426 (mostly occluded), alternately referred to as a "knife" or "blade." The cutting element 426 is aligned with and configured to traverse a guide track 428 (alternately referred to as a "defined" or "structured" pathway) defined longitudinally in one or both of the upper and lower jaws 210, 212. The cutting element 426 may be operatively coupled to the distal end of a drive rod 430 (alternately referred to as a "knife rod," "actuation rod," or "cutting rod") that extends longitudinally within the lumen 410 and passes through the wrist 206. Longitudinal movement (translation) of the drive rod 430 correspondingly moves the cutting element 426 within the guide track(s) 428 in the same direction.

The drive rod 430 may comprise a rigid or semi rigid elongate member, such as a rod or shaft (e.g., a hypotube, a hollow rod, a solid rod, etc.), a wire, a ribbon, a push cable, or any combination thereof. The drive rod 430 can be made from a variety of materials including, but not limited to, metal (e.g., tungsten, stainless steel, nitinol, etc.), a polymer, a composite material, or a combination thereof. The drive rod 430 may have a circular cross-section, but may alternatively exhibit a polygonal cross-section without departing from the scope of the disclosure.

Similar to the drive and jaw cables 408a-d, 418, the drive rod 430 may form part of the cable driven motion system and, therefore, may extend proximally from the cutting element 426 to the drive housing 208 (FIG. 2). The proximal end of the drive rod 430 may be operatively coupled to an actuation mechanism or device housed within the drive housing 208. Selective actuation of the corresponding drive input associated with the actuation mechanism or device will cause the drive rod 430 to move distally or proximally within the lumen 410, and correspondingly move the cutting element 426 in the same direction.

Figure 5:
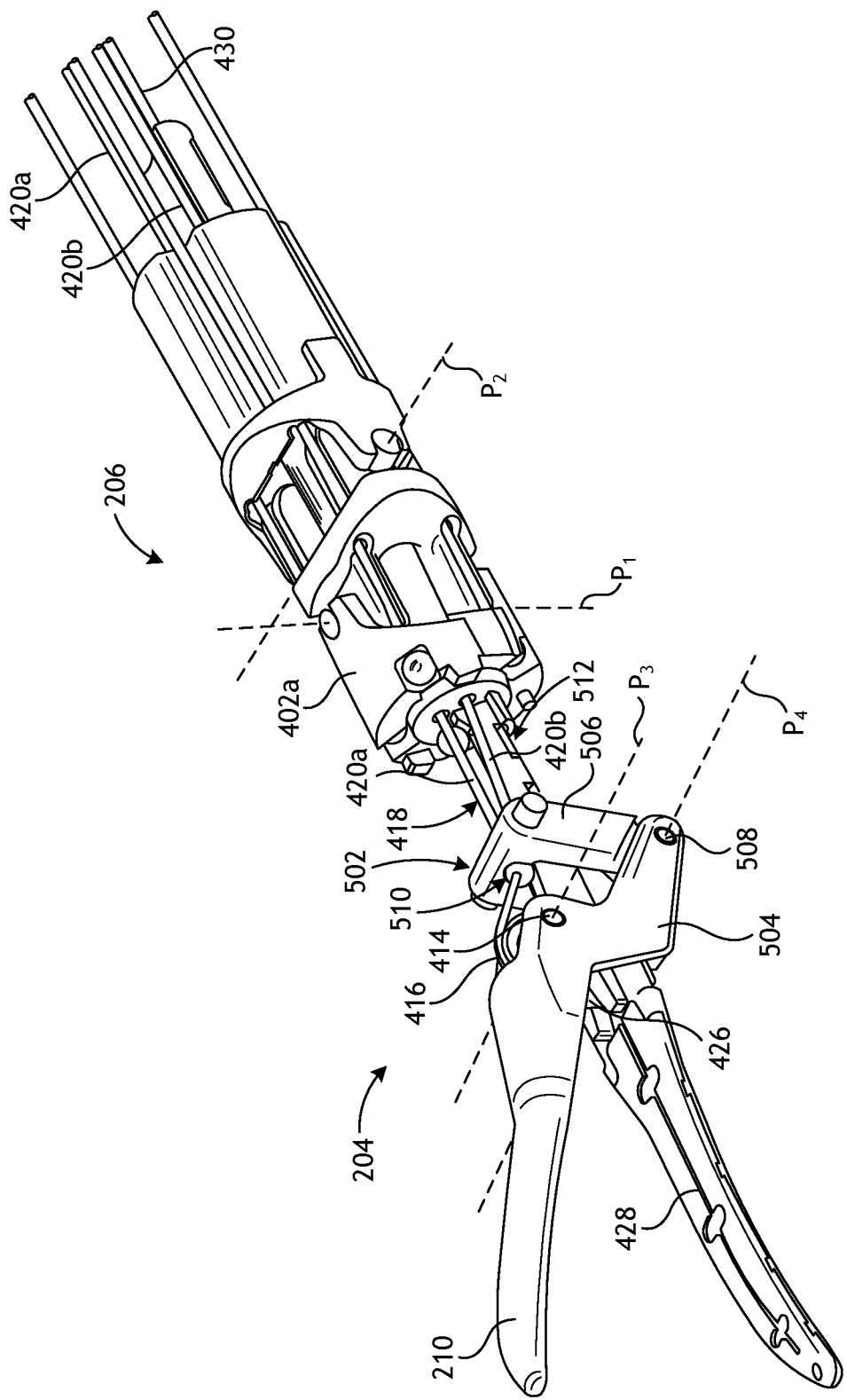
FIG. 5 is an isometric side view of the end effector of FIG. 4 in an open position, according to one or more embodiments.

FIG. 5 is an isometric side view of the end effector 204 in an open position, according to one or more embodiments. More particularly, FIG. 5 depicts the upper jaw 210 pivoted to the open position, and the lower jaw 212 (FIG. 4) is omitted to enable viewing of the internal components of the end effector 204. As illustrated, the end effector 204 includes a pivot link 502 operatively coupled to the upper jaw 210. More specifically, the upper jaw 210 provides or otherwise defines one or more legs 504 (one shown, one occluded) that are pivotably coupled to a corresponding one or more legs 506 (one shown, one occluded) of the pivot link 502 at a pivot axle 508. A fourth pivot axis $P_4$ extends through the pivot axle 508 and may be generally perpendicular (orthogonal) to the first pivot axis $P_1$ and parallel to the second and third pivot axes $P_2$, $P_3$.

The central pulley 416 (mostly occluded) is rotatably supported on the jaw axle 414, and the jaw cable 418 loops around the central pulley 416 and includes opposing ends 420a,b that extend proximally through the wrist 206. The jaw cable 418 may be operatively coupled to the pivot link 502 such that movement (i.e., longitudinal translation) of the jaw cable 418 correspondingly moves the pivot link 502. For example, a cable anchor 510 may be secured to or otherwise form part of one proximally extending end 420a,b of the jaw cable 418 and may help operatively couple the jaw cable 418 to the pivot link 502. In the illustrated embodiment, the cable anchor 510 comprises a ball crimp attached to the first end 420a and receivable within a socket defined by the pivot link 502. In other embodiments, however, the cable anchor 510 may alternatively include, but is not limited to, a weld, an adhesive attachment, a press fit engagement, or any combination of the foregoing and capable of being removably or permanently attached to the pivot link 502.

To move the jaws 210, 212 to the open position, the jaw cable 418 may be actuated to move the pivot link 502 distally, which may be done, for example, by pulling proximally on the second end 420b of the jaw cable 418 (alternately referred to as the "open cable"). As the pivot link 502 moves distally, the legs 506 of the pivot link 502 act on the legs 504 of the upper jaw 210 at the pivot axle 508. Distal movement of the pivot link 502 forces the legs 504 downward in rotation about the fourth pivot axis $P_4$, and downward movement of the legs 504 correspondingly causes upper jaw 210 to pivot about the third pivot axis $P_3$, similar to the operation of a two-bar linkage. As it pivots about the third pivot axis $P_3$, the upper jaw 210 is moved to the open position.

To move the upper jaw 210 back to the closed position, the jaw cable 418 may be actuated to move the pivot link 502 proximally, which may be done, for example, by pulling proximally on the first end 420a of the jaw cable 418 (alternately referred to as the "closure cable"). This causes the pivot link 502 to pull upward on the legs 504 of the upper jaw 210 in rotation about the fourth pivot axis $P_4$, and upward movement of the legs 504 correspondingly causes the upper jaw 210 to pivot about the third pivot axis $P_3$ and moves the upper jaw 210 back to the closed position.

In the illustrated embodiment, the end effector 204 may further include a longitudinal support structure 512 (partially colluded) that supports the drive rod 430 against buckling. As the cutting element 426 is advanced distally within the guide track(s) 428 to transect tissue grasped by the closed jaws 210, 212, the tissue will generate an opposing force (loading) in the proximal direction that resists distal movement of the cutting element 426. If the resistance load of the tissue surpasses the compressive capacity of the drive rod 430 in the distal direction, the drive rod 430 may buckle and the cutting operation will be compromised. The longitudinal support structure 512 may be configured to enhance or supplement the compressive capacity of the drive rod 430 and thereby mitigate buckling at or near the jaws 210, 212.

Figure 6A:
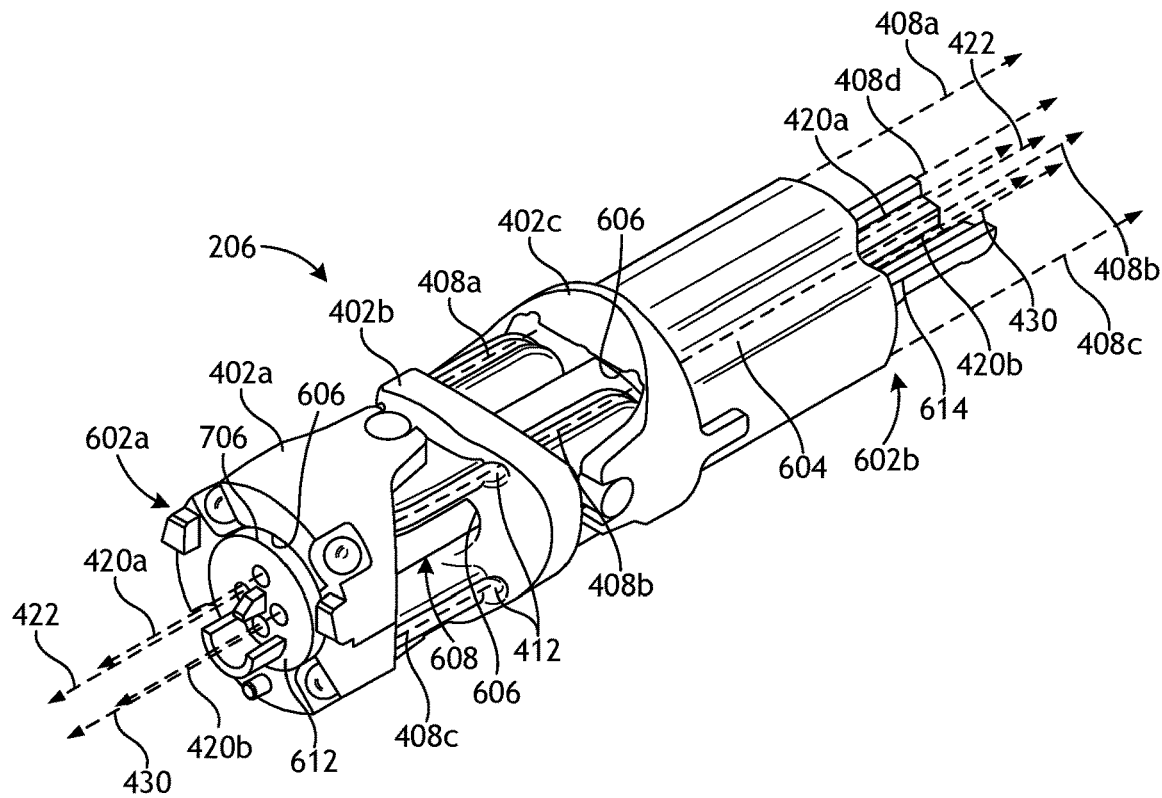
FIGS. 6A and 6B are enlarged isometric front and back views, respectively, of the wrist of FIGS. 4 and 5, according to one or more embodiments.
Figure 6B:
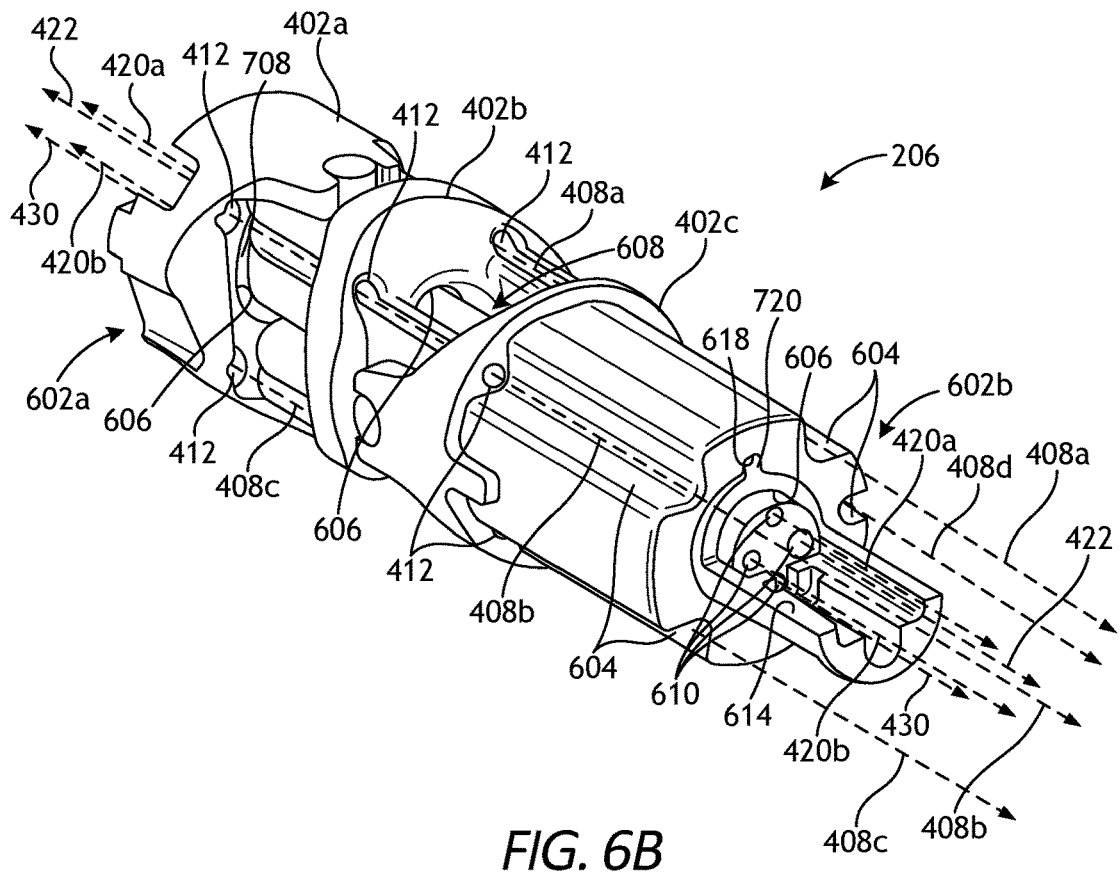

FIGS. 6A and 6B are enlarged isometric front and back views, respectively, of the wrist 206, according to one or more embodiments. The wrist 206 may have a first or "distal" end 602a and a second or "proximal" end 602b opposite the distal end 602a. The distal linkage 402a is positioned at the distal end 602a, the proximal linkage 402c is positioned at the proximal end 602b, and the intermediate linkage 402b interposes and operatively couples the distal and proximal linkages 402a,c. However, it is noted that embodiments are contemplated herein where the intermediate linkage 402b is omitted and the distal and proximal linkages 402a,c are alternatively directly coupled at a common axle.

The drive cables 408a-d, the electrical conductor 422, the first and second ends 420a,b of the jaw cable 418 (FIGS. 4 and 5), and the drive rod 430 are depicted in FIGS. 6A-6B as dashed lines for simplicity. As illustrated, the drive cables 408a-d pass through portions (e.g., apertures 412) of the wrist 206 and terminate at the distal linkage 402a. In some embodiments, the proximal linkage 402c may provide or otherwise define one or more longitudinal grooves 604 to accommodate each drive cable 408a-d. As illustrated, each groove 604 may be configured to receive a corresponding one of the drive cables 408a-d. The grooves 604 may be equidistantly-spaced or non-equidistantly spaced about the outer circumference of the proximal linkage 402c and otherwise aligned with the corresponding apertures 412 defined by the proximal linkage 402c. The grooves 604 may provide rounded edges to help reduce friction on the drive cables 408a-d during operation, and may help prevent the drive cables 408a-d from twisting or moving radially inward or outward during articulation of the wrist 206.

The wrist 206 may provide or otherwise define a central channel 606 that extends between the distal and proximal ends 602a,b. The electrical conductor 422, the first and second ends 420a,b of the jaw cable 418 (FIGS. 4 and 5), and the drive rod 430 may penetrate the wrist 206 by extending through the central channel 606. In embodiments where the wrist 206 includes the distal, intermediate, and proximal linkages 402a-c, as illustrated, corresponding portions of the central channel 606 may be cooperatively and successively defined by each linkage 402a-c. However, in embodiments where the wrist 206 includes only the distal and proximal linkages 402a,c, the central channel 606 may be defined cooperatively and successively by only the distal and proximal linkages 402a,c. The portions of the central channel 606 defined by each linkage 402a-c may coaxially align when the wrist 206 is non-articulated, but may move out of alignment once the wrist 206 is moved in articulation.

The wrist 206 may include a flexible member 608 arranged within the central channel 606 and extending at least partially between the first and second ends 602a-b of the wrist 206. As best seen in FIG. 6B, the flexible member 608 may provide or otherwise define one or more conduits 610 (four shown) that extend through the entire length of the flexible member 608. The conduits 610 may be configured to receive one or more of the electrical conductor 422, the first and second ends 420a,b of the jaw cable 418 (FIGS. 4 and 5), and the drive rod 430, collectively referred to herein as "central actuation members." Accordingly, one or more of the central actuation members may penetrate the wrist 206 by extending through the conduits 610 of the flexible member 608.

The flexible member 608 may be operatively coupled to the distal linkage 402a at its distal end, but may be free to move axially relative to the proximal linkage 402c at its proximal end. In some embodiments, for example, the wrist 206 may include a distal adapter 612 (FIG. 6A) and a proximal adapter 614 (FIG. 6B). The distal adapter 612 may be configured to operatively couple the flexible member 608 to the distal linkage 402a, and the proximal adapter 612 may be configured to support the flexible member 608 in sliding axial engagement with the proximal linkage 402c. In at least one embodiment, however, the proximal adapter 612 may be omitted and the flexible member 608 may directly contact the proximal linkage 402c in sliding engagement.

Figure 7A:
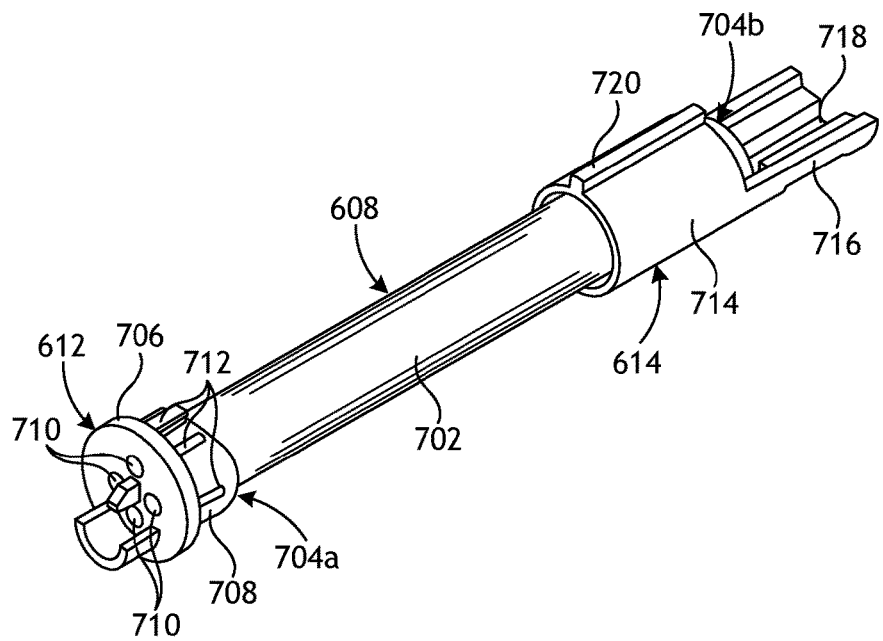
FIGS. 7A and 7B are isometric and exploded views, respectively, of the flexible member and the distal and proximal adapters of FIGS. 6A-6B, according to one or more embodiments.
Figure 7B:
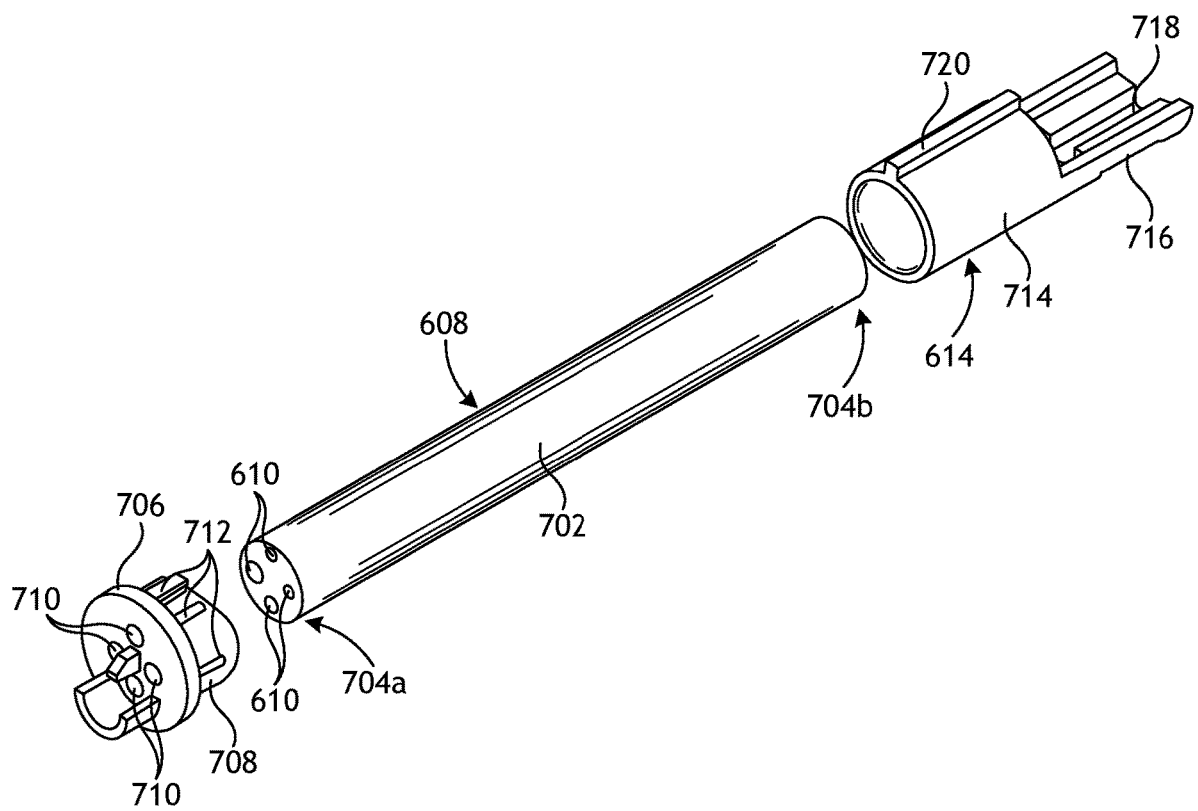

FIGS. 7A and 7B are isometric and exploded views, respectively, of the flexible member 608 and the distal and proximal adapters 612, 614, according to one or more embodiments. As illustrated, the flexible member 608 may comprise a generally cylindrical body 702 having a first or "distal" end 704a and a second or "proximal" end 704b opposite the distal end 704a. In some embodiments, as illustrated, the body 702 may exhibit a substantially circular cross-section, but may alternatively exhibit other cross-sectional shapes, such as polygonal (e.g., triangular, rectangular, etc.), oval, ovoid, or any combination thereof, without departing from the scope of the disclosure.

The flexible member 608 may be made of any flexible or semi-flexible material that allows the flexible member 608 to flex or bend when the wrist 206 (FIGS. 6A-6B) articulates. The material for the flexible member 608 may also exhibit low friction characteristics or may otherwise be lubricious, which may prove advantageous in minimizing friction caused by the central actuation members (e.g., the electrical conductor 422, the first and second ends 420a,b of the jaw cable 418, and the drive rod 430 of FIGS. 6A-6B) moving within the conduits 610. Furthermore, the material for the flexible member 608 may also exhibit good wear characteristics so the central actuation members do not inadvertently cut through the corresponding conduits 610 after repeated use. The diameter or size of each conduit 610 may be large enough to enable the central actuation members to move therein without substantive obstruction (friction), but small enough to support the central actuation members.

Suitable materials for the flexible member 608 include, but are not limited to, polytetrafluoroethylene (PTFE or TEFLON®), silicone, nylon, polyurethane (e.g., CARBOTHANE™), or any combination thereof. In at least one embodiment, the flexible member 608 may comprise an extrusion.

The distal adapter 612 may be made of a rigid or semi-rigid material including, but not limited to, a plastic, a metal, a composite material, and any combination thereof. Suitable materials for the distal adapter 612 include polyetherimide, polycarbonate, polystyrene, nylon, etc. In some embodiments, as illustrated, the distal adapter 612 may provide or otherwise define a radial shoulder 706 and a flange 708 that extends from the radial shoulder 706. The flange 708 may be sized to receive the distal end 704a of the flexible member 608. In other embodiments, however, the flange 708 may be omitted and the distal adapter 612 may nonetheless be coupled to the flexible member 608.

The distal adapter 612 may be coupled (fixed) to the distal end 704a of the flexible member 608 via a variety of attachment means. Suitable attachment means include, but are not limited to, bonding (e.g., an adhesive), welded (e.g., sonic or ultrasonic welding), overmolding the distal adapter 612 onto the distal end 704a, an interference or shrink fit, or any combination thereof.

The distal adapter 612 may define one or more or apertures 710 (four shown) configured to co-axially align with the conduits 610 of the flexible member 608. Accordingly, the central actuation members extending through the flexible member 608 (e.g., the electrical conductor 422, the first and second ends 420a,b of the jaw cable 418, and the drive rod 430 of FIGS. 6A-6B) may each exit the flexible member 608 at the apertures 710 of the distal adapter 612.

In some embodiments, the distal adapter 612 may provide one or more features 712 configured to mate with one or more corresponding features of the distal linkage 402a (FIGS. 6A-6B). In the illustrated embodiment, the features 712 are defined on the flange 708, but could alternatively be defined on any other portion of the distal adapter 612, without departing from the scope of the disclosure. Mating the features 712 of the distal adapter 612 with the corresponding features of the distal linkage 402a may help rotationally fix the distal end 704a of the flexible member 608 at the distal end 602a (FIGS. 6A-6B) of the wrist 206 (FIGS. 6A-6B).

The proximal adapter 614 may be made of a rigid or semi-rigid material including, but not limited to, a plastic, a metal, a composite material, and any combination thereof. Suitable materials for the proximal adapter 614 include polyetherimide, polycarbonate, polystyrene, nylon, etc. In the illustrated embodiment, the proximal adapter 614 provides a generally annular body 714 sized to receive the proximal end 704b of the flexible member 608. In some embodiments, the proximal end 704b may extend entirely through the annular body 714, but may alternatively extend only partially therethrough, without departing from the scope of the disclosure.

The proximal adapter 614 may be coupled (fixed) to the proximal end 704b of the flexible member 608 via a variety of attachment means. Suitable attachment means include, but are not limited to, bonding (e.g., an adhesive), welded (e.g., sonic or ultrasonic welding), overmolding the proximal adapter 614 onto the proximal end 704b, an interference or shrink fit, or any combination thereof.

In some embodiments, a flange 716 may extend proximally from the body 714 of the proximal adapter 614. The flange 716 may provide or define a groove 718 co-axially alignable with one of the conduits 610 defined through the flexible member 608 and sized to receive one of the central actuation members, such as the drive rod 430 (FIGS. 5 and 6A-6B). The groove 718 may prove advantageous in helping to prevent buckling of the drive rod 430 during operation.

In some embodiments, the proximal adapter 614 may provide one or more features 720 configured to mate with one or more corresponding features provided by the proximal linkage 402c (FIGS. 6A-6B). As discussed in more detail below, the feature 720 may comprise a longitudinal rib that may be configured to mate with a longitudinal channel of the proximal linkage 402c.

Referring again to FIGS. 6A-6B, in some embodiments, the distal adapter 612 may be partially received within the central channel 606 defined in the distal linkage 402a. More specifically, the flange 708 (see FIG. 6B) of the distal adapter 612 may extend into the central channel 606 until the radial shoulder 706 (see FIG. 6A) of the distal adapter 612 engages the distal end 602a of the wrist 206 and, more particularly, the distal linkage 402a. In some embodiments, one or more features (not shown) may be defined on the inner radial surface of the central channel 606 at the distal linkage 402a and configured to mate with the features 712 (FIGS. 7A-7B) of the distal adapter 612. Mating these features may help rotationally fix the distal adapter 612 relative to the distal end 602a (FIGS. 6A-6B) of the wrist 206 (FIGS. 6A-6B).

The distal adapter 612 may be arranged to interpose the lower jaw 212 (FIG. 4) and the distal linkage 402a within the assembly of the end effector 204 (FIGS. 4-5), thus restraining (trapping) the distal adapter 612 between the lower jaw 212 and the distal linkage 402a. Since the distal adapter 612 may be fixed to the distal end 704a (FIGS. 7A-7B) of the flexible member 608, restraining (trapping) the distal adapter 612 between the lower jaw 212 and the distal linkage 402a may correspondingly fix the flexible member 608 in place at the distal end 602a of the wrist 206.

Referring specifically to FIG. 6B, the proximal linkage 402c may provide or define a feature 618 sized and otherwise configured to receive (mate with) the feature 720 provided by the proximal adapter 614. In the illustrated embodiment, the feature 618 comprises a longitudinal channel, and the feature 720 comprises a longitudinal rib matable with the longitudinal channel. Mating the features 618, 720 may help rotationally fix the flexible member 608 to the proximal linkage 402c, but also allows the flexible member 608 to move longitudinally relative to the proximal linkage 402c. For example, as the wrist 206 articulates, the feature 720 of the proximal adapter 614 may slide relative to the feature 618 of the proximal linkage 402c. In some embodiments, however, the proximal adapter 614 may be omitted and the feature 720 may alternatively be provided by the flexible member 608, without departing from the scope of the disclosure. In other embodiments, the flexible member 608 may be molded or otherwise formed in a shape that lends itself to be rotationally fixed to the proximal linkage 402c, such as a square or "D" shape.

In example operation of the wrist 206, the drive cables 408a-d may be selectively actuated to cause the wrist 206 to articulate. As the wrist 206 articulates, the flexible member 608 is able to correspondingly bend or flex, and the central actuation members (e.g., the electrical conductor 422, the first and second ends 420a,b of the jaw cable 418, and the drive rod 430) will correspondingly move in the direction of articulation and thereby lengthen or shorten, depending on the bend direction of the flexible member 608. Extending the central actuation members through the conduits 610 of the flexible member 608 creates a defined and predictable pathway for each central actuation member. Moreover, fixing the flexible member 608 at or near the distal end 602a of the wrist 206 effectively provides a fixed and known location where the central actuation members exit the wrist 206. Furthermore, as the wrist 206 changes articulation positions, the central actuation members correspondingly change length and the flexible member 608 is able to slide longitudinally relative to the proximal linkage 402c at the proximal end 602b of the wrist 206. The rotationally fixed orientation of the flexible member 608 helps prevent the central actuation members from twisting, which maintains predictable locations for each central actuation member.

Embodiments disclosed herein include:

A. An articulable wrist for an end effector that includes a distal linkage provided at a distal end of the articulable wrist, a proximal linkage provided at a proximal end of the articulable wrist, a central channel cooperatively defined by the distal and proximal linkages and extending between the distal and proximal ends, a flexible member arranged within the central channel and having a first end operatively coupled to the distal linkage and a second end axially movable relative to the proximal linkage, and one or more conduits defined in the flexible member to receive one or more central actuation members extending through the flexible member.

B. A surgical tool that includes a drive housing, an elongate shaft that extends from the drive housing, an end effector arranged at an end of the elongate shaft, an articulable wrist that interposes the end effector and the elongate shaft, the articulable wrist including a distal linkage provided at a distal end of the articulable wrist and operatively coupled to the end effector, a proximal linkage provided at a proximal end of the articulable wrist and operatively coupled to the elongate shaft, a central channel cooperatively defined by the distal and proximal linkages and extending between the distal and proximal ends, and a flexible member arranged within the central channel and having a first end operatively coupled to the distal linkage and a second end axially movable relative to the proximal linkage. The surgical tool further including one or more central actuation members extending from the drive housing and through the flexible member via one or more conduits defined in the flexible member.

C. A method of operating a surgical tool that includes positioning the surgical tool adjacent a patient for operation, the surgical tool including a drive housing, an elongate shaft that extends from the drive housing, an end effector arranged at an end of the elongate shaft, and a wrist that interposes the end effector and the elongate shaft and includes a distal linkage provided at a distal end of the wrist and operatively coupled to the end effector, a proximal linkage provided at a proximal end of the wrist and operatively coupled to the elongate shaft, a central channel cooperatively defined by the distal and proximal linkages and extending between the distal and proximal ends, a flexible member arranged within the central channel and having a first end operatively coupled to the distal linkage and a second end axially movable relative to the proximal linkage, and one or more conduits defined in the flexible member to receive one or more central actuation members extending through the flexible member. The method further including articulating the wrist and simultaneously bending the flexible member within the central channel.

Each of embodiments A, B, and C may have one or more of the following additional elements in any combination: Element 1: further comprising an intermediate linkage interposing the distal and proximal linkages and defining a portion of the central channel. Element 2: wherein the one or more central actuation members are selected from the group consisting of an electrical conductor, first and second ends of a jaw cable, and a drive rod. Element 3: further comprising a distal adapter coupled to the first end of the flexible member and engageable with the distal linkage to operatively couple the flexible member to the distal linkage. Element 4: wherein the distal adapter provides a flange that receives the first end of the flexible member. Element 5: wherein the distal adapter defines one or more or apertures co-axially alignable with the one or more conduits such that the one or more central actuation members also extend through the one or more apertures. Element 6: further comprising a proximal adapter coupled to the second end of the flexible member and slidingly engageable with the proximal linkage. Element 7: wherein the proximal adapter provides an annular body that receives the second end of the flexible member. Element 8: wherein the flexible member comprises a material selected from the group consisting of polytetrafluoroethylene, silicone, nylon, polyurethane, and any combination thereof.

Element 9: further comprising an intermediate linkage interposing the distal and proximal linkages and defining a portion of the central channel. Element 10: further comprising a distal adapter coupled to the first end of the flexible member and engageable with the distal linkage to operatively couple the flexible member to the distal linkage. Element 11: wherein the distal adapter defines one or more or apertures co-axially alignable with the one or more conduits such that the one or more central actuation members also extend through the one or more apertures. Element 12: further comprising a proximal adapter coupled to the second end of the flexible member and slidingly engageable with the proximal linkage. Element 13: wherein the flexible member comprises a material selected from the group consisting of polytetrafluoroethylene, silicone, nylon, polyurethane, and any combination thereof. Element 14: further comprising one or more drive cables extending from the drive housing and extending through a corresponding one or more apertures defined by the articulable wrist to cause articulation of the articulable wrist.

Element 15: wherein articulating the wrist comprises actuating one or more drive cables extending from the drive housing, wherein the one or more drive cables extend through a corresponding one or more apertures defined by the wrist. Element 16: further comprising operatively coupling the first end of the flexible member to the distal linkage with a distal adapter fixed to the first end of the flexible member. Element 17: further comprising slidingly engaging to the second end of the flexible member against the proximal linkage with a proximal adapter coupled to the second end of the flexible member.

By way of non-limiting example, exemplary combinations applicable to A, B, and C include: Element 3 with Element 4; Element 3 with Element 5; Element 3 with Element 6; Element 6 with Element 7; Element 10 with Element 11; and Element 10 with Element 12.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An articulable wrist for an end effector, comprising:
a distal linkage provided at a distal end of the articulable wrist;
a proximal linkage provided at a proximal end of the articulable wrist;
a central channel cooperatively defined by the distal and proximal linkages and extending between the distal and proximal ends;
a flexible member arranged within the central channel and having a first end operatively coupled to the distal linkage and a second end axially movable relative to the proximal linkage;
a distal adapter fixed to an end of the flexible member and matable with the distal linkage to rotationally fix the flexible member at the distal end of the articulable wrist, wherein a portion of the distal adapter extends into the central channel through the distal linkage; and
one or more conduits defined in the flexible member to receive one or more central actuation members extending through the flexible member.

2. The articulable wrist of claim 1, further comprising an intermediate linkage interposing the distal and proximal linkages and defining a portion of the central channel.

3. The articulable wrist of claim 1, wherein the one or more central actuation members are selected from the group consisting of an electrical conductor, first and second ends of a jaw cable, and a drive rod.

4. The articulable wrist of claim 1, wherein the distal adapter provides:
a radial shoulder engageable with the distal linkage at the distal end of the articulable wrist; and
a flange that extends from the radial shoulder and into the central channel via the distal linkage and receives the first end of the flexible member.

5. The articulable wrist of claim 1, wherein the distal adapter defines one or more or apertures co-axially alignable with the one or more conduits such that the one or more central actuation members also extend through the one or more apertures.

6. The articulable wrist of claim 1, further comprising a proximal adapter coupled to the second end of the flexible member and slidingly engageable with the proximal linkage.

7. The articulable wrist of claim 6, wherein the proximal adapter provides an annular body that receives the second end of the flexible member.

8. The articulable wrist of claim 1, wherein the flexible member comprises a material selected from the group consisting of polytetrafluoroethylene, silicone, nylon, polyurethane, and any combination thereof.

9. A surgical tool, comprising:
a drive housing;
an elongate shaft that extends from the drive housing;
an end effector arranged at an end of the elongate shaft;
an articulable wrist that interposes the end effector and the elongate shaft, the articulable wrist including:
a distal linkage provided at a distal end of the articulable wrist and operatively coupled to the end effector;
a proximal linkage provided at a proximal end of the articulable wrist and operatively coupled to the elongate shaft;
a central channel cooperatively defined by the distal and proximal linkages and extending between the distal and proximal ends;
a flexible member arranged within the central channel and having a first end operatively coupled to the distal linkage and a second end axially movable relative to the proximal linkage; and
a distal adapter fixed to an end of the flexible member and matable with the distal linkage to rotationally fix the flexible member at the distal end of the articulable wrist, wherein a portion of the distal adapter extends into the central channel through the distal linkage; and
one or more central actuation members extending from the drive housing and through the flexible member via one or more conduits defined in the flexible member.

10. The surgical tool of claim 9, further comprising an intermediate linkage interposing the distal and proximal linkages and defining a portion of the central channel.

11. The surgical tool of claim 9, wherein the distal adapter defines one or more or apertures co-axially alignable with the one or more conduits such that the one or more central actuation members also extend through the one or more apertures.

12. The surgical tool of claim 9, further comprising a proximal adapter coupled to the second end of the flexible member and slidingly engageable with the proximal linkage.

13. The surgical tool of claim 9, wherein the flexible member comprises a material selected from the group consisting of polytetrafluoroethylene, silicone, nylon, polyurethane, and any combination thereof.

14. The surgical tool of claim 9, further comprising one or more drive cables extending from the drive housing and extending through a corresponding one or more apertures defined by the articulable wrist to cause articulation of the articulable wrist.

15. The surgical tool of claim 9, wherein the distal adapter includes:
a radial shoulder engageable with the distal linkage at the distal end of the articulable wrist; and
a flange that extends from the radial shoulder and into the central channel via the distal linkage and receives the first end of the flexible member.

16. A method of operating a surgical tool, comprising:
positioning the surgical tool adjacent a patient for operation, the surgical tool including a drive housing, an elongate shaft that extends from the drive housing, an end effector arranged at an end of the elongate shaft, and a wrist that interposes the end effector and the elongate shaft and includes:
a distal linkage provided at a distal end of the wrist and operatively coupled to the end effector;
a proximal linkage provided at a proximal end of the wrist and operatively coupled to the elongate shaft;
a central channel cooperatively defined by the distal and proximal linkages and extending between the distal and proximal ends;
a flexible member arranged within the central channel and having a first end operatively coupled to the distal linkage and a second end axially movable relative to the proximal linkage;
a distal adapter fixed to an end of the flexible member and matable with the distal linkage to rotationally fix the flexible member at the distal end of the articulable wrist, wherein a portion of the distal adapter extends into the central channel through the distal linkage; and
one or more conduits defined in the flexible member to receive one or more central actuation members extending through the flexible member; and
articulating the wrist and simultaneously bending the flexible member within the central channel.

17. The method of claim 16, wherein articulating the wrist comprises actuating one or more drive cables extending from the drive housing, wherein the one or more drive cables extend through a corresponding one or more apertures defined by the wrist.

18. The method of claim 16, further comprising slidingly engaging the second end of the flexible member against the proximal linkage with a proximal adapter coupled to the second end of the flexible member.

19. The method of claim 16, wherein the distal adapter includes:
- a radial shoulder engageable with the distal linkage at the distal end of the articulable wrist; and
- a flange that extends from the radial shoulder and into the central channel via the distal linkage and receives the first end of the flexible member.

\* \* \* \* \*